United States Patent [19]
Shikhman et al.

[11] Patent Number: 5,947,989
[45] Date of Patent: Sep. 7, 1999

[54] METHOD AND APPARATUS FOR TRANSMYOCARDIAL REVASCULARIZATION

[75] Inventors: Oleg Shikhman, Fairfield; James Correia, Shelton, both of Conn.

[73] Assignee: United States Surgical Corporation, Norwalk, Conn.

[21] Appl. No.: 08/764,417

[22] Filed: Dec. 12, 1996

[51] Int. Cl.$^6$ .................................................. A61B 17/00
[52] U.S. Cl. .......................................... 606/180; 606/170
[58] Field of Search ............................... 606/1, 108, 170, 606/171, 159, 180, 7; 600/562–571

[56] References Cited

U.S. PATENT DOCUMENTS

| | | |
|---|---|---|
| 3,087,486 | 4/1963 | Kilpatrick . |
| 3,821,510 | 6/1974 | Muncheryan . |

(List continued on next page.)

FOREIGN PATENT DOCUMENTS

| | | |
|---|---|---|
| 0 144 764 A2 | 6/1985 | European Pat. Off. . |
| 0196519 | 3/1986 | European Pat. Off. . |
| 0266858A1 | 5/1988 | European Pat. Off. . |
| 0189329 | 7/1989 | European Pat. Off. ................. 606/7 |
| 0 325 836 A2 | 8/1989 | European Pat. Off. . |
| 0481684 | 10/1991 | European Pat. Off. . |
| 0553576 | 1/1992 | European Pat. Off. . |
| 0 515 867 A3 | 12/1992 | European Pat. Off. . |
| 0669107 | 2/1995 | European Pat. Off. . |
| 0737486 | 10/1996 | European Pat. Off. . |
| 0738518 | 10/1996 | European Pat. Off. . |
| 3911796 A1 | 10/1990 | Germany . |
| WO 80/01238 | 6/1980 | WIPO . |
| WO 9314711 | 8/1993 | WIPO . |
| WO 9315672 | 8/1993 | WIPO . |
| WO 9315676 | 8/1993 | WIPO . |
| WO 9315677 | 8/1993 | WIPO . |
| WO 9320767 | 10/1993 | WIPO . |
| WO 9320768 | 10/1993 | WIPO . |
| WO 9401374 | 1/1994 | WIPO . |
| WO 9402077 | 2/1994 | WIPO . |
| WO 9410922 | 5/1994 | WIPO . |
| WO 9410923 | 5/1994 | WIPO . |
| WO 9414383 | 7/1994 | WIPO . |
| WO 9426184 | 11/1994 | WIPO . |
| WO 9505212 | 2/1995 | WIPO . |
| WO 9635469 | 11/1996 | WIPO . |
| WO 9639962 | 12/1996 | WIPO . |
| WO 9639964 | 12/1996 | WIPO . |
| WO 9639965 | 12/1996 | WIPO . |
| WO 9707735 | 3/1997 | WIPO . |
| WO 9713468 | 4/1997 | WIPO . |
| WO 9718768 | 5/1997 | WIPO . |
| WO 9725101 | 7/1997 | WIPO . |

OTHER PUBLICATIONS

Hardy, et al., "Regional Myocardial Blood Flow and Cardiac Mechanics in Dog Hearts with $CO_2$ Laser–Induced Intramyocardial Revascularization", *Basic Research in Cardiology*, 85:179–197 (1990).

Mirhoseini, et al., "Direct Myocardial Revascularization: Preliminary Experience", Lasers in Cardiovascular Medicine and Surgery: Fundamentals and Techniques, (Abela, G., ed.), Kluwer Academic Publishers, 385–395.

(List continued on next page.)

*Primary Examiner*—Michael Buiz
*Assistant Examiner*—William Lewis

[57] ABSTRACT

A method for performing transmyocardial revascularization (TMR) comprises the steps of creating an incision in an outer portion of heart tissue of a patient and creating a channel in the patient's myocardium through the incision by advancing a channel creating device into the myocardium beyond the depth of the incision to remove myocardial tissue without removing all outer portion heart tissue coinciding with the channel. As a result, the remaining outer portion tissue acts as a cap to reduce bleeding from the channel subsequent to removal of the channel creating device. The cap may be in the form of an annular flap of myocardial/epicardial tissue. The channel creating device used to create the channel with the method can be either a mechanical coring device or an advancing lasing device.

14 Claims, 14 Drawing Sheets

U.S. PATENT DOCUMENTS

| | | |
|---|---|---|
| 4,266,548 | 5/1981 | Davi . |
| 4,269,174 | 5/1981 | Adair . |
| 4,311,138 | 1/1982 | Sugarman . |
| 4,336,809 | 6/1982 | Clark . |
| 4,461,305 | 7/1984 | Cibley . |
| 4,469,098 | 9/1984 | Davi . |
| 4,564,011 | 1/1986 | Goldman . |
| 4,640,296 | 2/1987 | Schnepp-Pesch et al. . |
| 4,658,817 | 4/1987 | Hardy . |
| 4,696,209 | 9/1987 | Meller et al. . |
| 4,785,815 | 11/1988 | Cohen . |
| 4,830,460 | 5/1989 | Goldenberg . |
| 4,860,743 | 8/1989 | Abela . |
| 4,862,887 | 9/1989 | Weber et al. . |
| 4,913,142 | 4/1990 | Kittrell et al. . |
| 4,928,695 | 5/1990 | Goldman et al. . |
| 4,940,061 | 7/1990 | Terwilliger et al. . |
| 4,985,028 | 1/1991 | Isner et al. . |
| 4,997,431 | 3/1991 | Isner et al. . |
| 5,037,421 | 8/1991 | Boutacoff et al. . |
| 5,048,538 | 9/1991 | Terwilliger et al. . |
| 5,093,877 | 3/1992 | Aita et al. . |
| 5,104,393 | 4/1992 | Isner et al. . |
| 5,106,386 | 4/1992 | Isner et al. . |
| 5,109,830 | 5/1992 | Cho . |
| 5,111,832 | 5/1992 | Saksena . |
| 5,147,354 | 9/1992 | Boutacoff et al. . |
| 5,188,632 | 2/1993 | Goldenberg . |
| 5,196,004 | 3/1993 | Sinofsky . |
| 5,251,641 | 10/1993 | Xavier ................................. 600/567 |
| 5,257,989 | 11/1993 | Celaya et al. . |
| 5,300,066 | 4/1994 | Manoukian et al. . |
| 5,304,171 | 4/1994 | Gregory et al. . |
| 5,312,396 | 5/1994 | Feld et al. . |
| 5,324,300 | 6/1994 | Elias et al. . |
| 5,346,497 | 9/1994 | Simon et al. . |
| 5,380,316 | 1/1995 | Aita et al. . |
| 5,389,096 | 2/1995 | Aita et al. . |
| 5,405,348 | 4/1995 | Anspach, Jr. et al. . |
| 5,423,330 | 6/1995 | Lee . |
| 5,437,660 | 8/1995 | Johnson et al. . |
| 5,488,958 | 2/1996 | Topel et al. . |
| 5,505,211 | 4/1996 | Ohto et al. . |
| 5,511,556 | 4/1996 | DeSantis . |
| 5,549,601 | 8/1996 | McIntyre et al. . |
| 5,591,159 | 1/1997 | Taheri . |
| 5,615,690 | 4/1997 | Giurtino et al. . |
| 5,620,439 | 4/1997 | Abela et al. . |
| 5,651,785 | 7/1997 | Abela et al. . |
| 5,672,170 | 9/1997 | Cho et al. . |
| 5,700,259 | 12/1997 | Negus et al. . |
| 5,703,985 | 12/1997 | Owyang . |
| 5,713,894 | 2/1998 | Murphy-Chutorian et al. . |
| 5,738,680 | 4/1998 | Mueller et al. . |
| 5,782,823 | 7/1998 | Mueller . |

OTHER PUBLICATIONS

Mirhoseini, et al., "Myocardial Revascularization by Laser: A Clinical Report", *Lasers in Surgery and Medicine*, 3:241–245 (1983).

Mirhoseini, et al., "Laser Applications in Thoracic and Cardiovascular Surgery", *Medical Instrumentation*, 17:401–403 (Nov.–Dec. 1982).

Mirhoseini, et al., "New Concepts in Revascularization of the Myocardium", The Annals of Thoracic Surgery, vol. 45, No. 4, Apr., 1988.

Jeevanandam, et al., "Myocardial Revascularization By Laser–induced Channels", Surgical Forum XLI, pp. 225–227, Oct. 1990.

Mirhoseini, et al., "Lasers in Cardiothoracic Surgery$^a$", Chapter 21, pp. 216–232.

Mirhoseini, et al., "Clinical and Histological Evaluation of Laser Myocardial Revascularization", Journal of Clinical Laser Medicine & Surgery, pp. 73–78, Jun. 1990.

Mirhoseini, "Laser Revascularizationof the Heart", pp. 296–303.

Mirhoseini, et al., "Transventricular Revascularization by Laser", Lasers in Surgery and Medicine, 2:187–198 (1982).

Dean T. Mason, M.D., American Heart Journal, vol. 112, No. 1, Jul. 1986.

Mirhoseini, et al., "Clinical Report: Laser Myocardial Revascularization", Lasers in Surgery and Medicine, 6:459–461 (1986).

Mirhoseini, et al., "Laser Revascularization of the Heart", SPIE, vol. 357, Lasers in Medicine and Surgery pp. 98–103, (1982).

Mirhoseini, et al., "Revascularization of the Heart by Laser", Journal of Microsurgery, pp. 253–260, Jun. 1981.

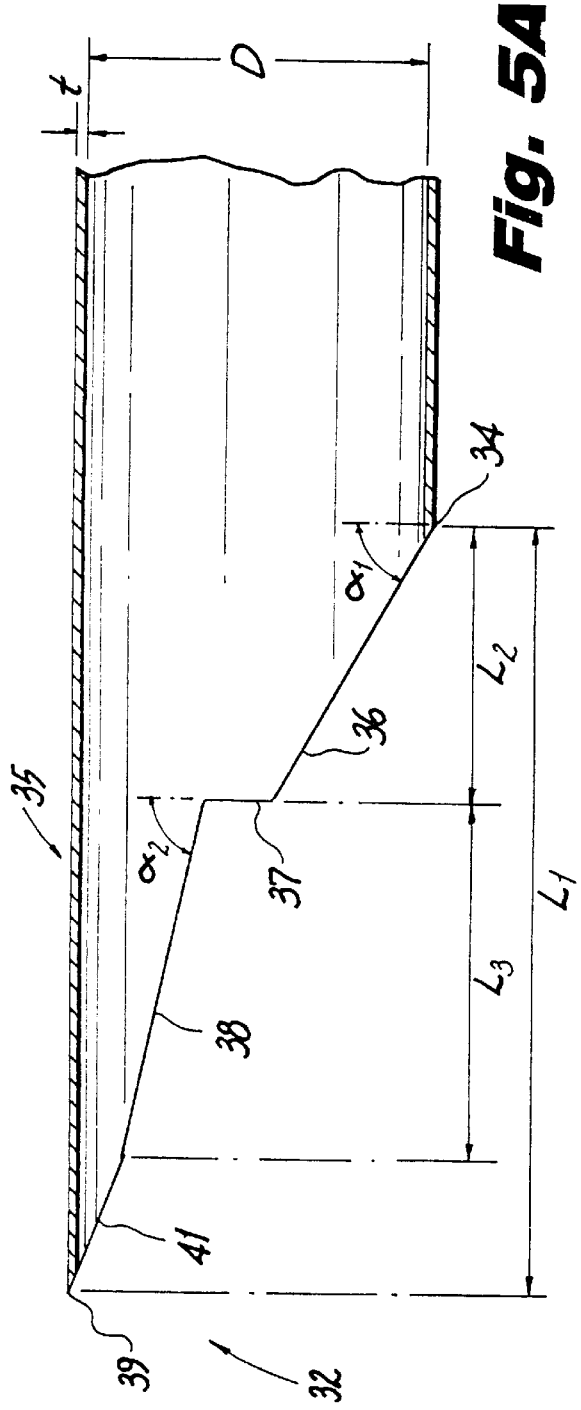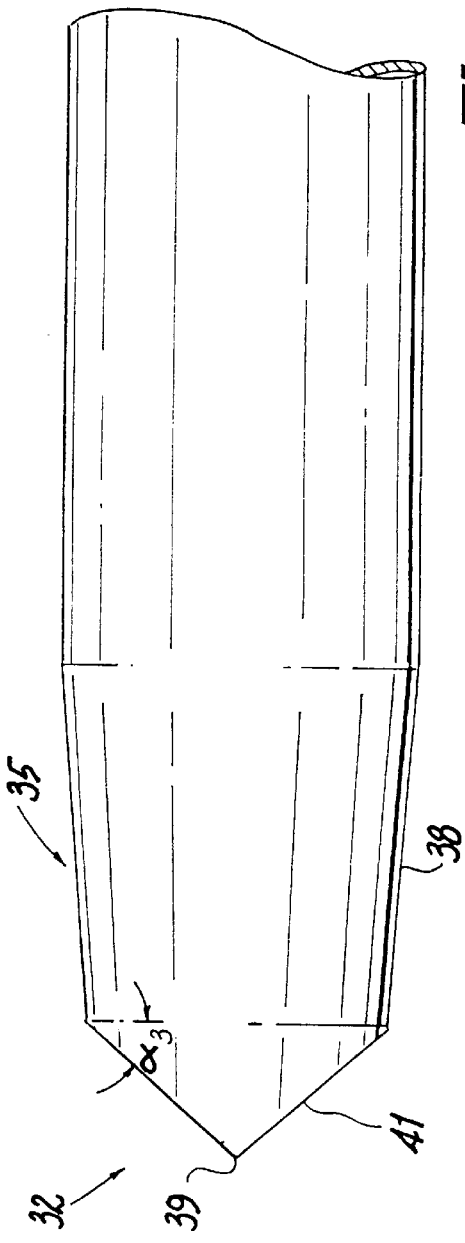

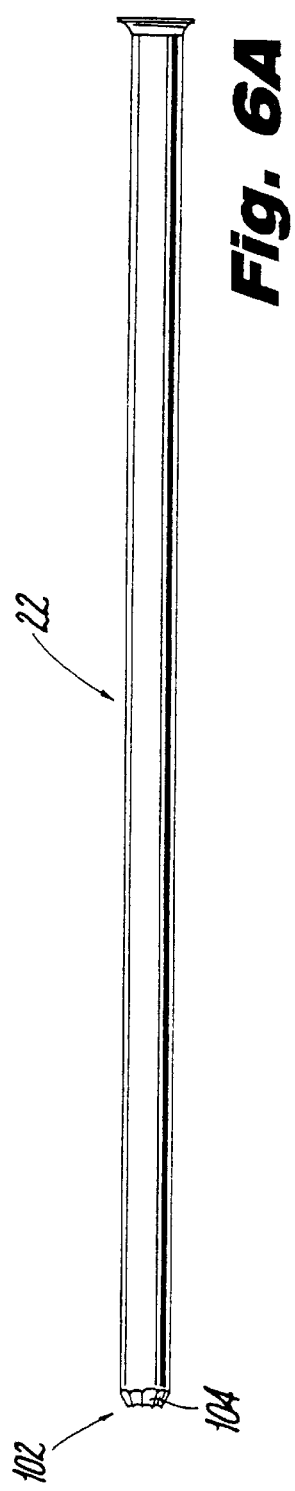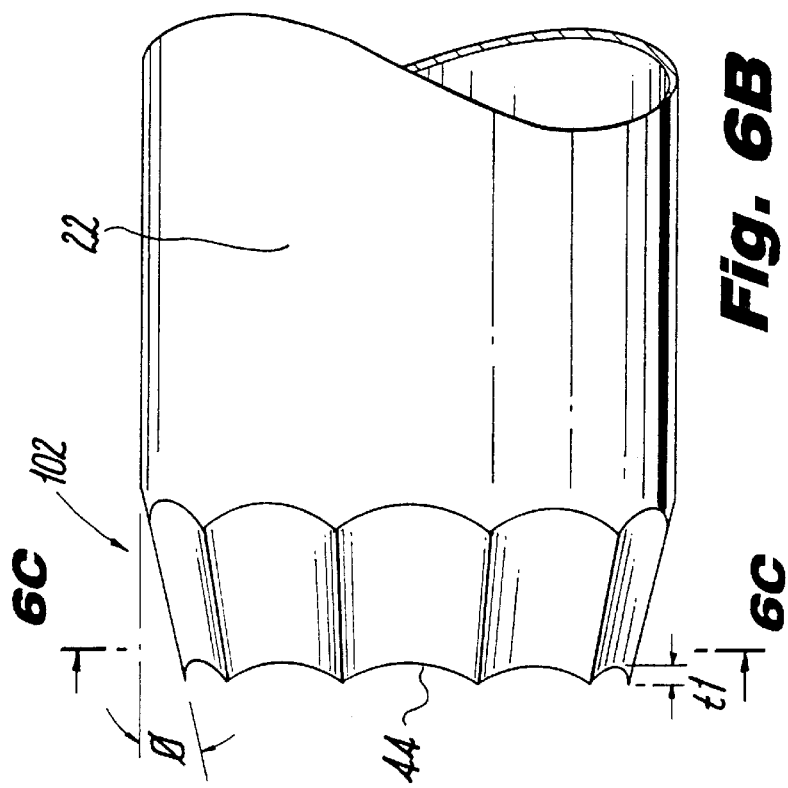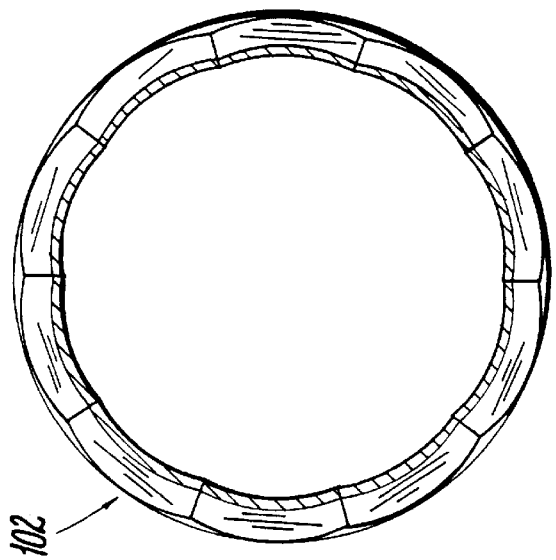

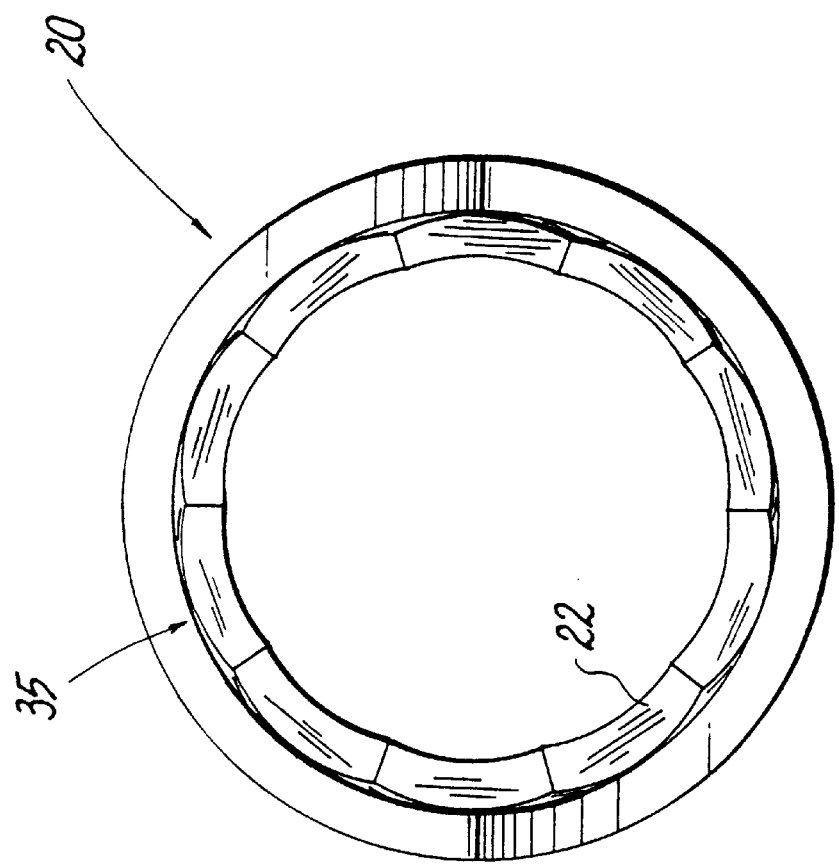

METHOD AND APPARATUS FOR TRANSMYOCARDIAL REVASCULARIZATION

BACKGROUND

1. Technical Field

The present disclosure relates to an improved method for transmyocardial revascularization (TMR) and apparatus for implementing the same.

2. Background of the Related Art

TMR is a known procedure for producing channels of small diameters within the myocardium, which channels extend into the ventricle. Such channels are believed to facilitate delivery of blood directly from the ventricle to oxygen starved areas of the heart. TMR is typically used on patients with ischemic heart disease who are not candidates for coronary artery bypass or percutaneous transluminal angioplasty.

During a TMR procedure, typically dozens of channels are created from the epicardium, through the myocardium and endocardium and into the ventricle, with each channel being of sufficiently small diameter such that the end portions of the channels at the epicardium can be closed by blood clotting. The channels are preferably created by employing either a mechanical coring apparatus or an advancing lasing device. With either technique, an important objective is to produce channels that remain patent in the long term and which do not close up due to fibrosis and/or scarring.

With current TMR procedures the technique for stopping the bleeding from each channel at the epicardium after channel formation entails applying pressure to the opening of the just-formed channel. Pressure is typically applied by the finger of the surgeon or assistant during open heart surgery, or with a laparoscopic instrument when the procedure is performed laparoscopically. In either case, since pressure is applied to each channel opening for at least several seconds, and it is impractical to begin forming another channel until the bleeding is stopped from the previous channel, the overall TMR procedure wherein typically dozens of channels are formed is undesirably prolonged by the time expended on applying pressure to each channel.

Accordingly, a need exists for a TMR procedure wherein the time spent to stop the blood flow from each of the individual transmyocardial channels is reduced or eliminated, thereby increasing the likelihood of success of each operation and saving lives.

SUMMARY

The present disclosure is directed to a method for performing transmyocardial revascularization (TMR) that alleviates the aforementioned problems in prior art methods. The method comprises the steps of creating an incision in an outer portion of heart tissue of a patient and creating a channel in the patient's myocardium through the incision by advancing a channel creating device into the myocardium beyond the depth of the incision to remove myocardial tissue without removing all outer portion heart tissue coinciding with the channel. As a result, the remaining outer portion tissue acts as a cap to reduce bleeding from the channel subsequent to removal of the channel creating device. The cap may be in the form of an annular flap of myocardial/epicardial tissue.

The channel creating device used to create the channel with the method can be either a mechanical coring device or an advancing lasing device.

The present disclosure also relates to apparatus for implementing the above TMR method. In one embodiment, an apparatus comprises a mechanical coring device having a tubular coring member for creating a channel within a patient's myocardium, and a flap creating member integrated with the mechanical coring device for creating a flap of heart tissue at an outer portion of the channel to reduce bleeding therefrom.

In another embodiment, an apparatus for performing TMR comprises a lasing device having a laser ablation member for creating a channel within a patient's myocardium by ablating myocardial tissue and correspondingly advancing into the myocardium, and a flap creating member integrated with the lasing device for creating a flap of heart tissue at an outer portion of the channel to likewise reduce bleeding.

Advantageously, with the present disclosure methods and apparatus, the adjoining interface between the cap or flap of heart tissue thus formed, and the proximal myocardial tissue defines a very narrow opening. Hence, blood clotting can occur rapidly at the interface. As a result, the time expended for the step of applying pressure to the channel opening following formation of each channel is substantially reduced as compared to prior art methods. Alternatively, the present disclosure may allow the time-consuming pressure-applying step to be eliminated altogether from the procedure.

BRIEF DESCRIPTION OF THE DRAWINGS

Various preferred embodiments are described herein with reference to the drawings, wherein:

FIGS. 5A and 5B are cross-sectional and rear views, respectively, of the flap creating member portion of FIG. 4;

FIGS. 6A–6C are various views of the coring member portion of FIG. 4;

FIGS. 7A-7B show assembly of the coring/flap creating assembly;

DETAILED DESCRIPTION

Figure 1:
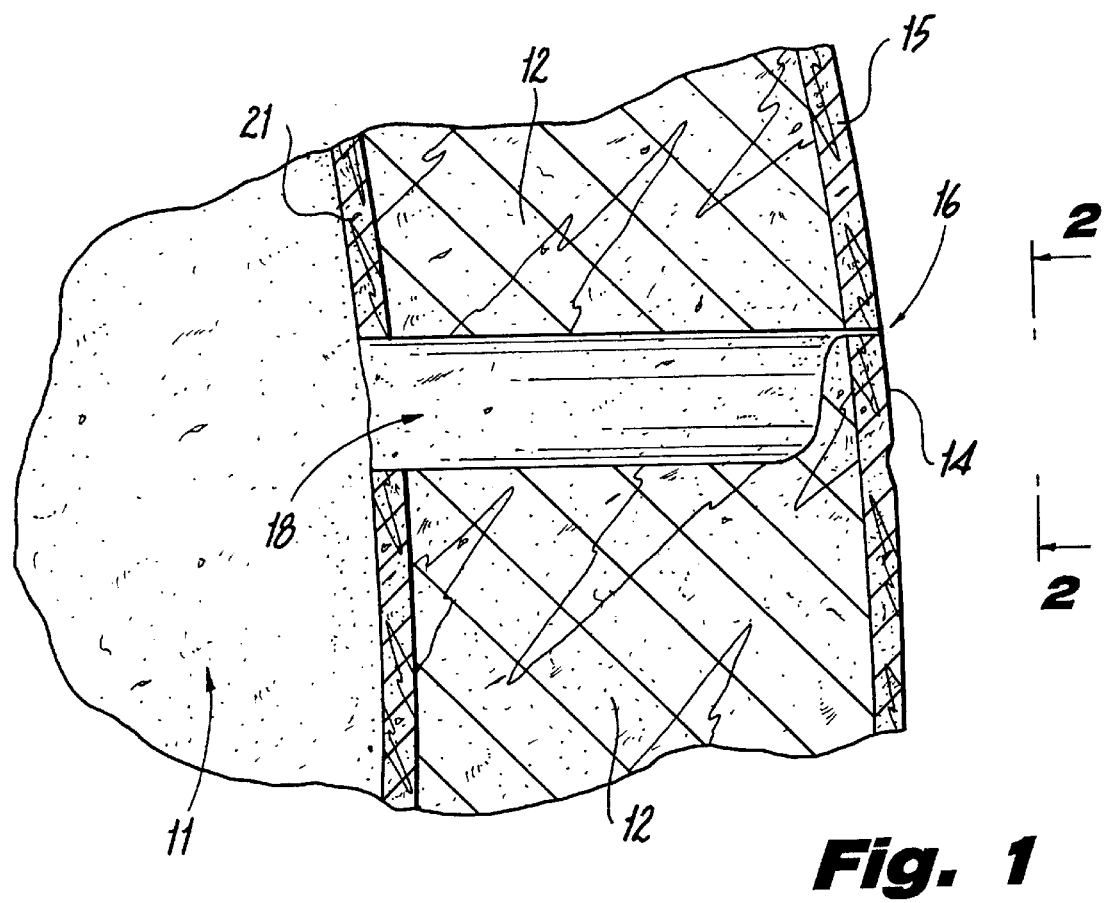
FIG. 1 is a cross-sectional view of an illustrative transmyocardial channel formed in accordance with the present disclosure.

Preferred embodiments of TMR methods and apparatus will now be described in detail with reference to the drawings, in which like reference numerals designate identical or corresponding elements.

Referring to FIG. 1, a cross-sectional view of a transmyocardial channel 18 which is formed by methods and apparatus in accordance with the present disclosure is shown. Channel 18 is generally cylindrical and extends from epicardium 15 through myocardium 12 and endocardium 21 into ventricle 11. The channel is "capped" by means of a flap 14 of heart tissue comprising epicardial tissue 15 sandwiched with myocardial tissue 12. Flap 14 is sealed to the rest of myocardium 12 and epicardium 15 at adjoining interface 16 by blood clotting. As is apparent from FIGS. 1 and 2, flap 14 has a shape resembling a tapered disk that is less than 360 degrees in annular extent. However, it is understood that it may be possible to form flap 14 in other shapes, such as a circular "plug" unitary with the myocardium along a full 360 degree perimeter with a centralized incision. The following description will describe the "flap" embodiment; however, it is understood that the disclosure is not so limited.

In the prior art, transmyocardial channels that are formed with an advancing mechanical coring or laser ablation member, are formed without a flap or cap at the outer portion of the channel (i.e., in the vicinity of the epicardium). As such, the channels are sealed or capped by means of blood clotting extending across the entire diameter of the channel opening at the epicardium. Since the surface area of each such blood clot is excessively large, it is necessary to apply pressure to the opening to speed up clot formation.

Advantageously, in accordance with the present disclosure wherein flap 14 is formed, blood clotting is only necessary at the adjoining interface (i.e., incision) 16 to re-attach flap 14 to the rest of myocardium 12/epicardium 15. Hence, the surface area of blood clotting is substantially reduced and bleeding stops much faster for a given diameter channel as compared to the prior art. Indeed, it may be possible to totally eliminate the pressure-applying step, whereby dozens of channels can be created in rapid succession. In addition, it may be feasible, if desired, to form wider diameter channels than is practically realizable in the prior art.

Figure 3:
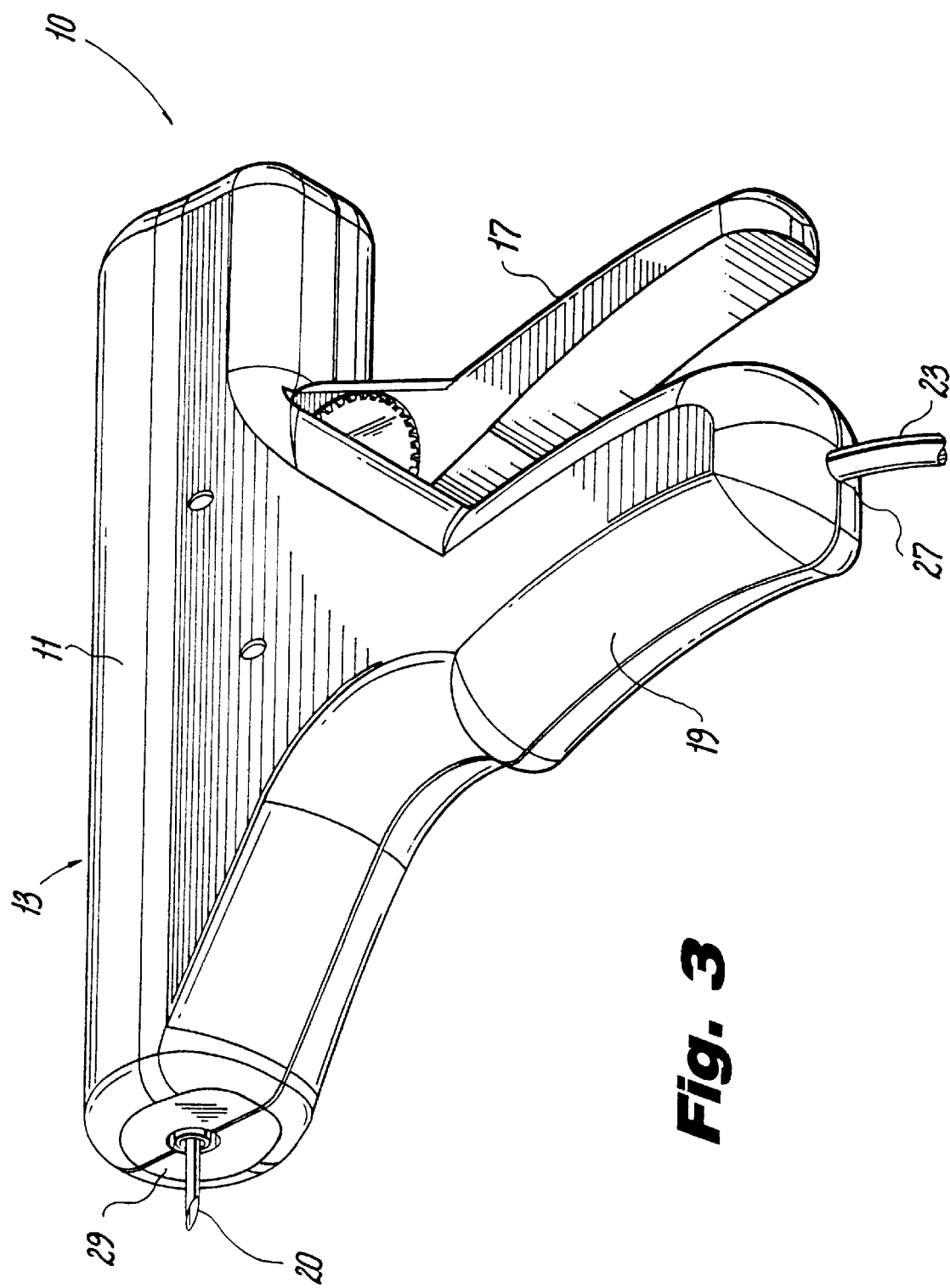
FIG. 3 shows an embodiment of a device for mechanical channel coring and flap creation in accordance with the disclosure.

Referring now to FIG. 3, as illustrative mechanical coring/flap creating device 10 is shown which can be employed to produce channel 18 with flap 14 during open heart surgery. Device 10 is a modified design of a mechanical coring device described in detail in commonly assigned, copending U.S. patent application Ser. No. 08/650,485, filed on May 13, 1996 entitled CORING DEVICE AND METHOD, to Pacala et al. Pacala et al. describes a mechanical coring device for coring body tissue to define reproducible patent channels by utilizing a coring member that is rotatable and linearly advanceable at coordinated, predetermined rates.

As shown in FIG. 3 of the present disclosure, device 10 differs from the coring device of Pacala et al. by utilizing a coring/flap creating assembly 20, described in further detail below, rather than just a coring member to core channels. Other features of device 10 are similar to those described in Pacala et al. For example, housing 13 includes an elongated body portion 11 defining the longitudinal axis of device 10 and a stationary handle 19 projecting from elongated body portion 11. A movable trigger 17 is pivotally connected to housing 13 adjacent stationary handle 19 forming a pistol type grip. An opening 27 allows passage of power supply cable 23 into the housing to power the linear advancement and rotation of the coring number of assembly 20 when trigger 17 is depressed. Surface 29 is brought into contact with the epicardium during the channel-forming procedure.

Figure 4:
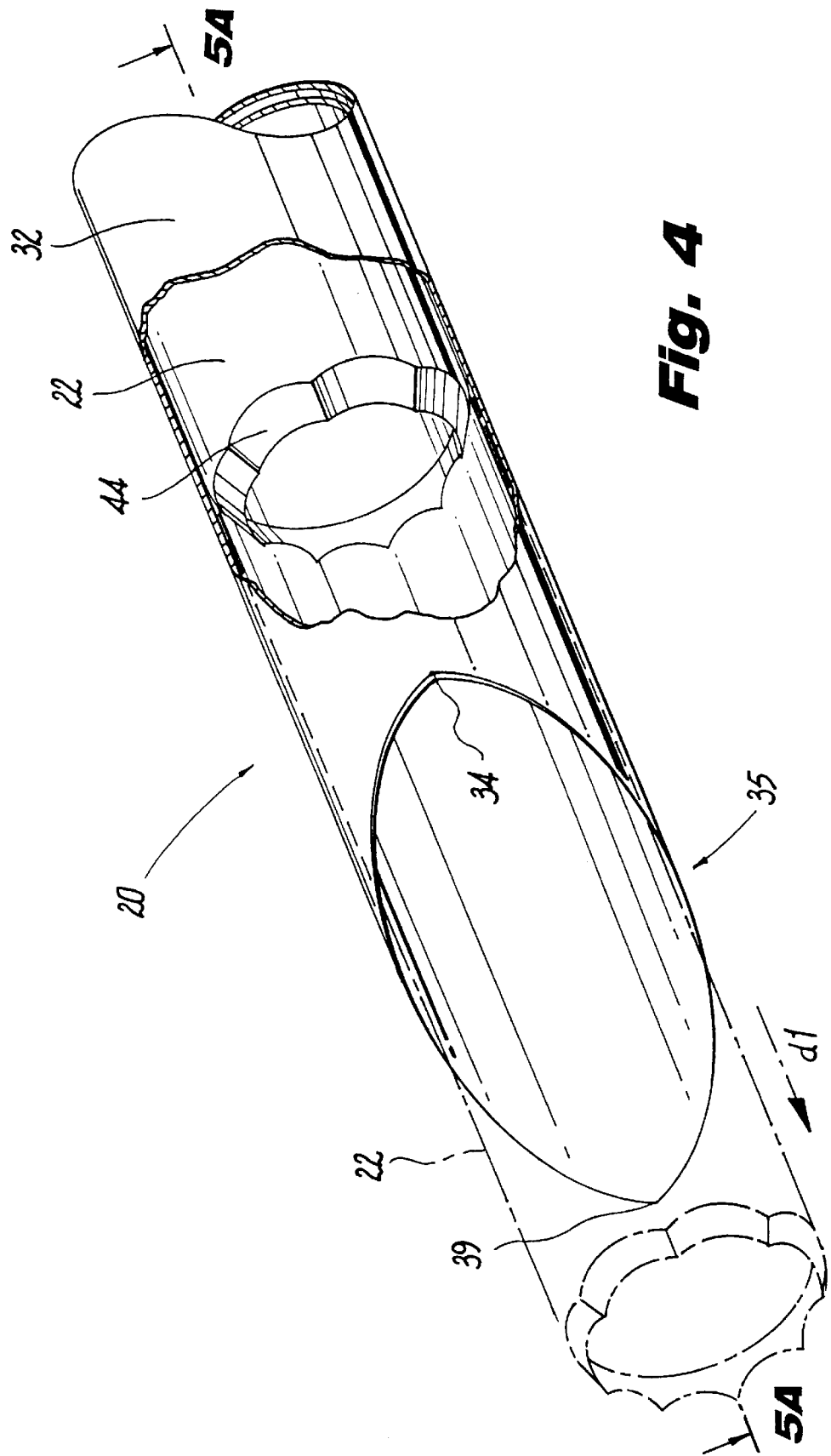
FIG. 4 is a perspective view of a coring/flap creating assembly used in the device of FIG. 3.

Referring to FIG. 4, an embodiment of coring/flap creating assembly 20 is illustrated in a perspective view. Assembly 20 comprises an outer flap creating member 32 and a coring member 22 inside member 32, where both members are preferably shaped as tubular cylinders. Coring member 22 cores tissue with a serrated annular edge 44 and moves translationally with respect to member 32 in direction d1 during the coring operation. Flap creating member 32 has a cutting portion 35 which is of a beveled shape defining a peak 39 and trough 34. In a storage position, with trigger 17 of FIG. 3 at rest, members 22 and 32 are preferably retracted back into housing 13 so that the sharp cutting edges do not protrude, thereby preventing accidental injury.

A preferred configuration for the cutting portion of flap creating member 32 is shown more clearly in the cross-sectional and rear views of FIGS. 5A and 5B, respectively. Referring to FIG. 5A, a first beveled portion 36 extends from 34 to peak or tip 39 and can have an angle a1 in the range of 15–35°. Second beveled portions 41 which are seen more clearly in FIG. 5B. Beveled portions 41 are generallysymetrical about peak 39 and intersect to form peak 39.

The thickness t of the perimeter wall of member 32 is selected in correspondence with diameter D. For example, for a diameter D of about 2 mm, t may be in the range of 0.05 mm to 0.3 mm. (Diameter D is slightly larger than the outer diameter of the coring member 22). Thickness t should be sufficiently large to enable heart tissue to be pushed aside as the cutting end 35 penetrates. Sufficient heart tissue needs to be pushed aside to prevent all of the heart tissue that is coincident with the channel from being cored away as coring member 22 advances to bore the channel, whereby the desired flap will be formed.

Figure 7A:
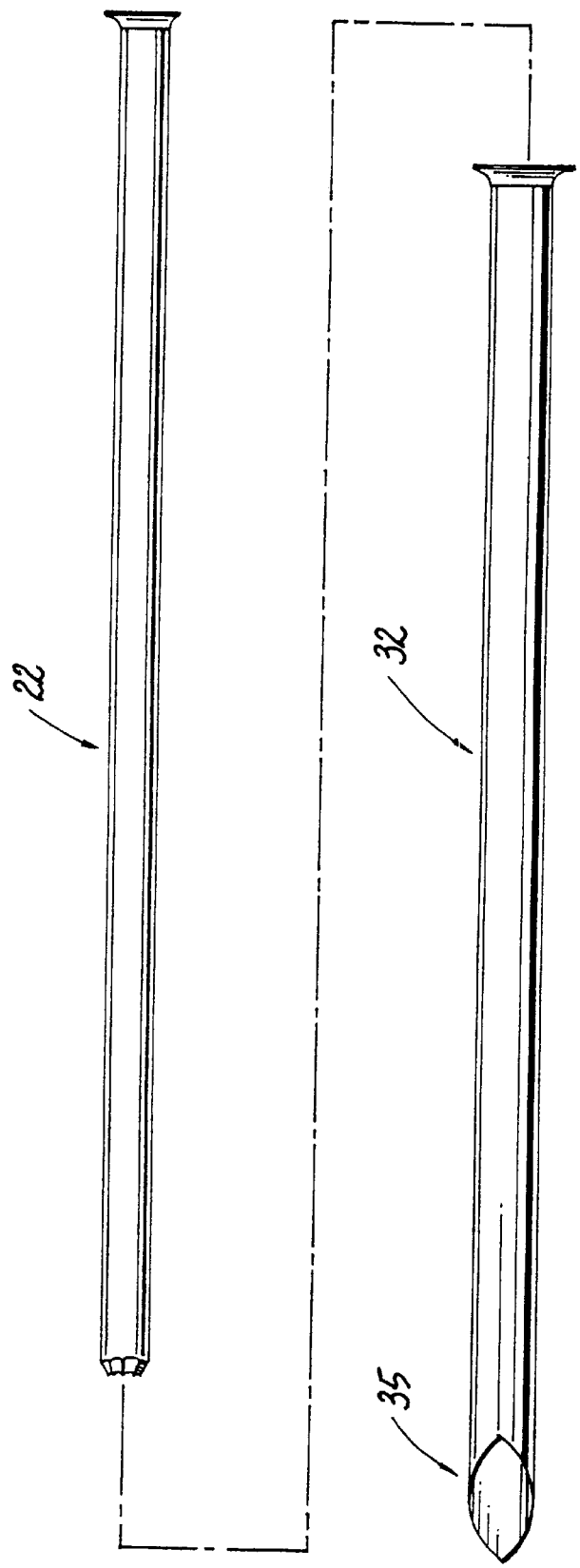

With reference to FIGS. 6A–6C, coring member 22 is an elongated tubular member having a central throughbore and a coring end 102 in the form of serrated annular edge 44. Coring end 102 is formed from a plurality of spaced serrations formed at an angle $\phi$ with respect to the longitudinal axis of coring member 22. The serrations are preferably flat cuts as shown in FIG. 6C but can also be contoured such as, for example, being concave or convex. Each serration has a tool depth t1 which preferably ranges from about 0.05 mm to about 0.20 mm. The number of serrations preferably ranges from about 4 to about 20. FIG. 7A illustrates assembly of coring member 22 within flap creating member 32; FIG. 7B shows an end view of the assembly 20.

Exemplary values of tool depth t and core diameter in relation to the number of serrations are recited in Pacala et al. cited above. That patent application also discloses exemplary rotational speeds and advancement rates for the core member and details of how to integrate the coring member with the coring device to effectuate the same.

It will be understood that the coring device can be modified by one skilled in the art to incorporate the flap creating member 32 disclosed herein. The modification amounts to adding the additional tubular member 32 surrounding the coring member to realize coring/flap creating assembly 20 (FIG. 1 herein) with adequate support therefor within housing 11, and preferably, with means for retracting the cutting portion 35 as discussed above to prevent injury. Optionally, the modification enables automatic extraction of the cutting portion 35 to a predetermined distance either by initial depression of trigger 17 or by depression of an additional triggering button on the housing. The inclusion of an automatic extraction mechanism will enable the operator to place the device on the surface of the epicardium, depress the automatic extraction trigger to cause flap creating member 32 to incise and penetrate the epicardium, and then core the channel by depressing trigger 17.

Figure 2:
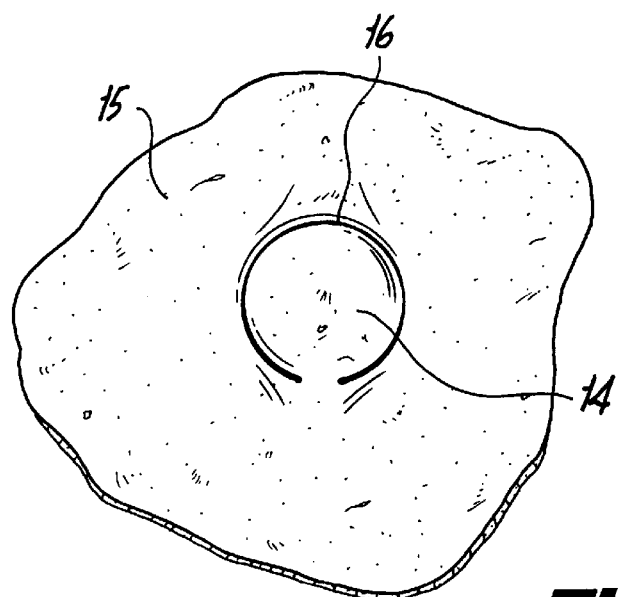
FIG. 2 is the end view AA of FIG. 1.
Figure 8:
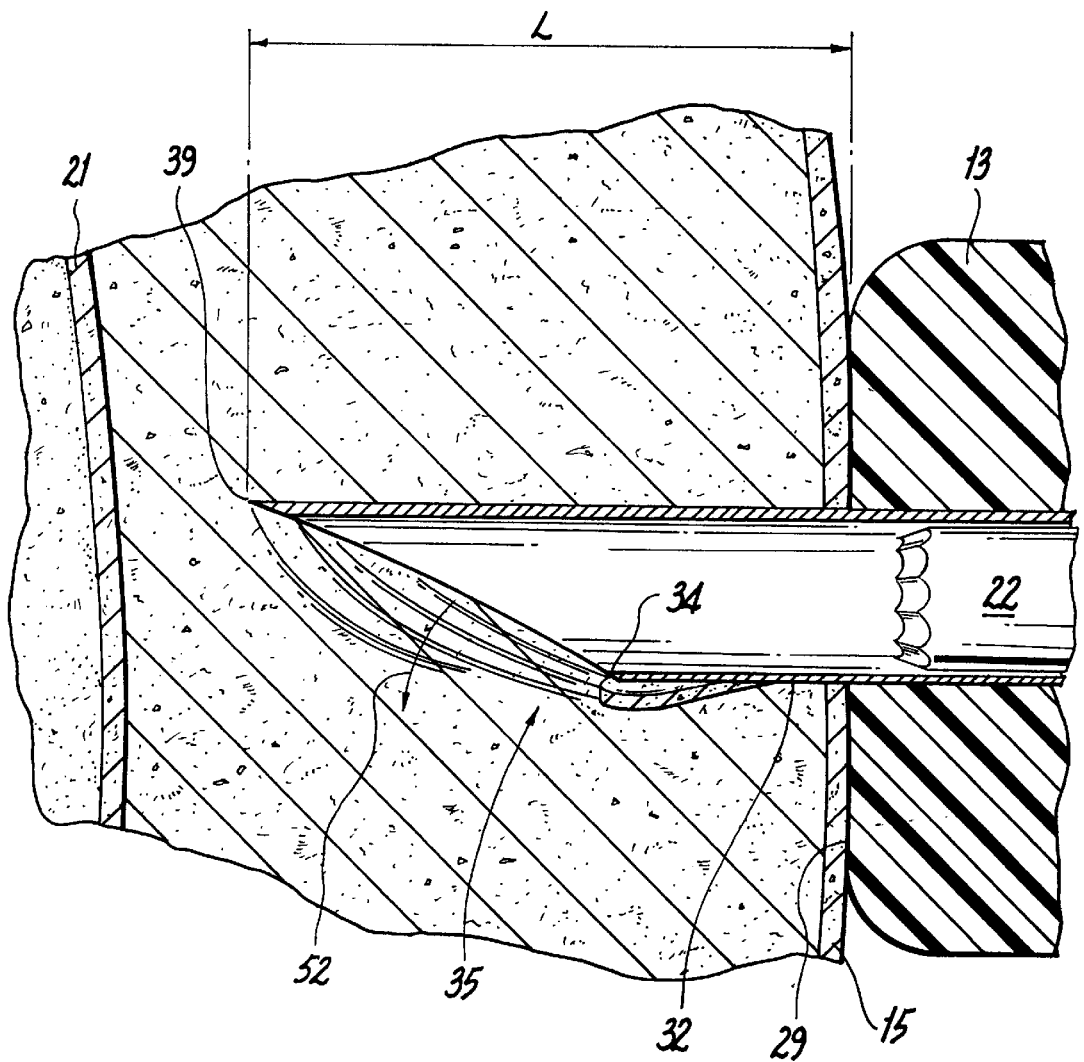
FIGS. 8 and 9 are cross-sectional views of a coring/flap creating assembly creating a channel in accordance with the present disclosure.
Figure 9:
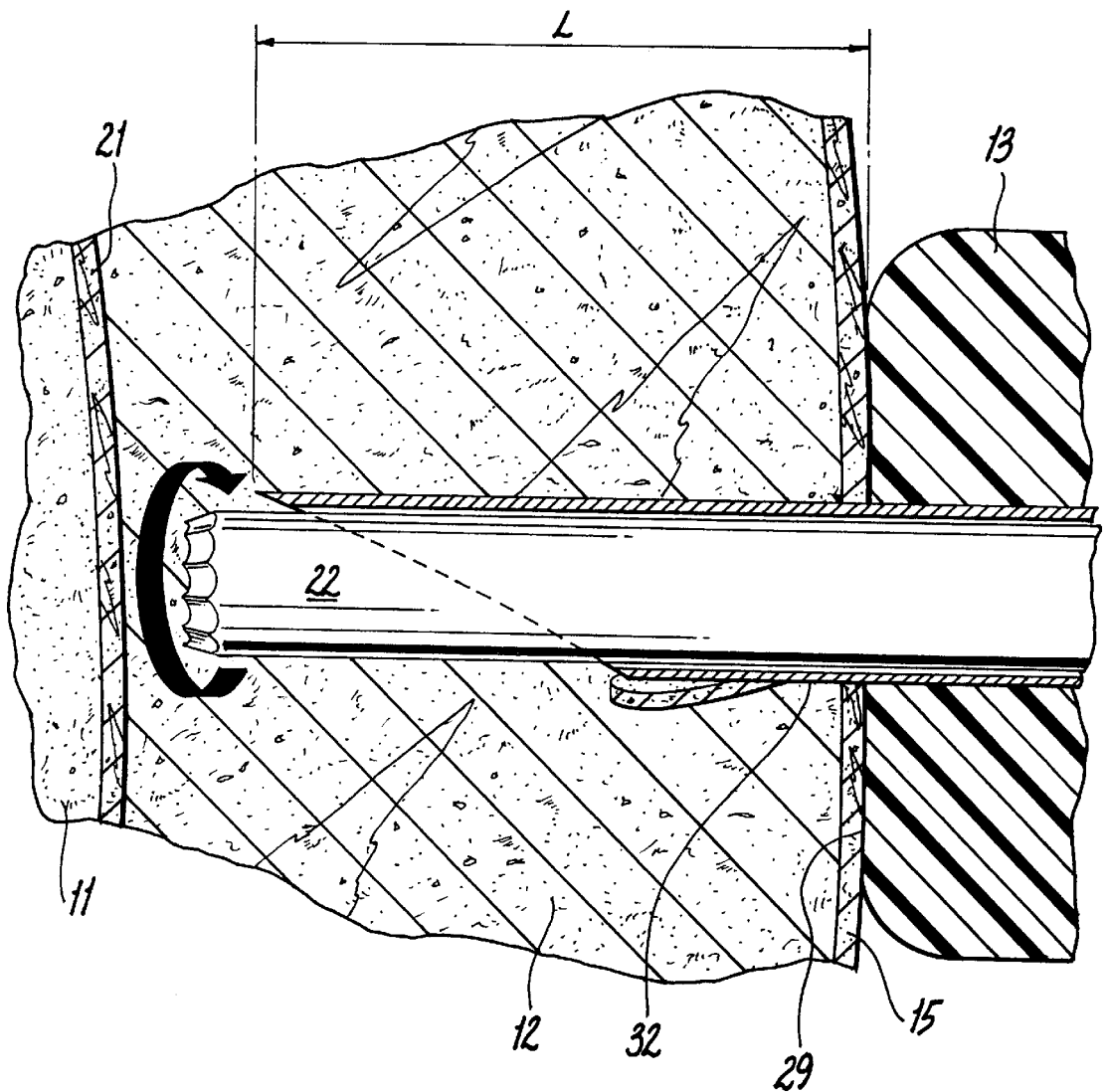
Figure 10:
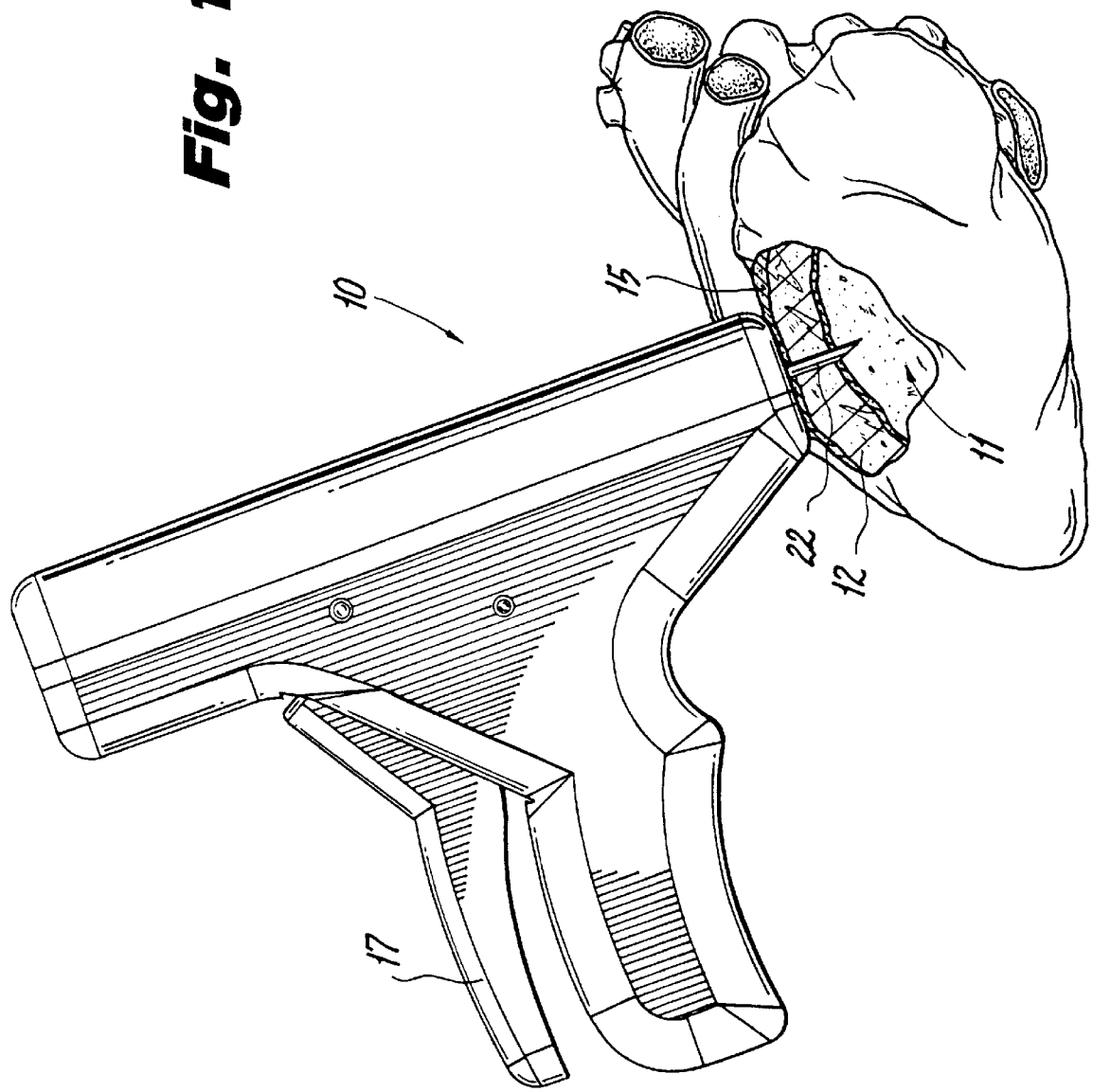
FIG. 10 illustrates the device of FIG. 3 creating a transmyocardial channel.

Referring now to the cross sectional illustration of FIG. 8, a TMR procedure in accordance with the present disclosure is initiated by inserting cutting portion 35 of flap creating member 32 a predetermined distance L into a patient's myocardium 12, whether by automatic extraction or manual insertion of cutting portion 35. If manual insertion is employed, surface 29 of the housing of device 10 can operate as a stop to prevent excessive penetration. With an automatic extraction embodiment, surface 29 is first placed against the epicardium and then cutting edge 35 is extracted by the distance L. In any case, as cutting portion 35 is inserted, an annular incision is created which separates both the epicardium and myocardium. As cutting portion 35 penetrates, heart tissue that is separated by the incision is pushed aside by the walls of the cutting portion, as indicated by arrows 52, and compresses against the adjoining tissue.

once the cutting portion is inserted to the desired position corresponding to the distance L, it is maintained in that position while the coring operation is performed. As shown in FIG. 9, coring member 22 is rotated and advanced through flap creating member 32 in order to core out the channel. Preferably, the coring member is simultaneously advanced and rotated at predetermined coordinated rates in order to form a channel having a substantially uniform diameter. Myocardial and endocardial tissue that is cored is drawn backwards through the hollow center of coring member 22. After member 22 reaches the ventricle, as shown in FIG. 10, coring member 22 is withdrawn by releasing trigger 17. Flap creating member 32 is then withdrawn, whereby the myocardial/endocardial tissue that was pushed aside recoils to its original position, resulting in the channel 18 with flap 14 as shown in FIGS. 1 and 2. The operator can then immediately begin producing another channel without applying pressure to the previously formed channel.

Figure 11:
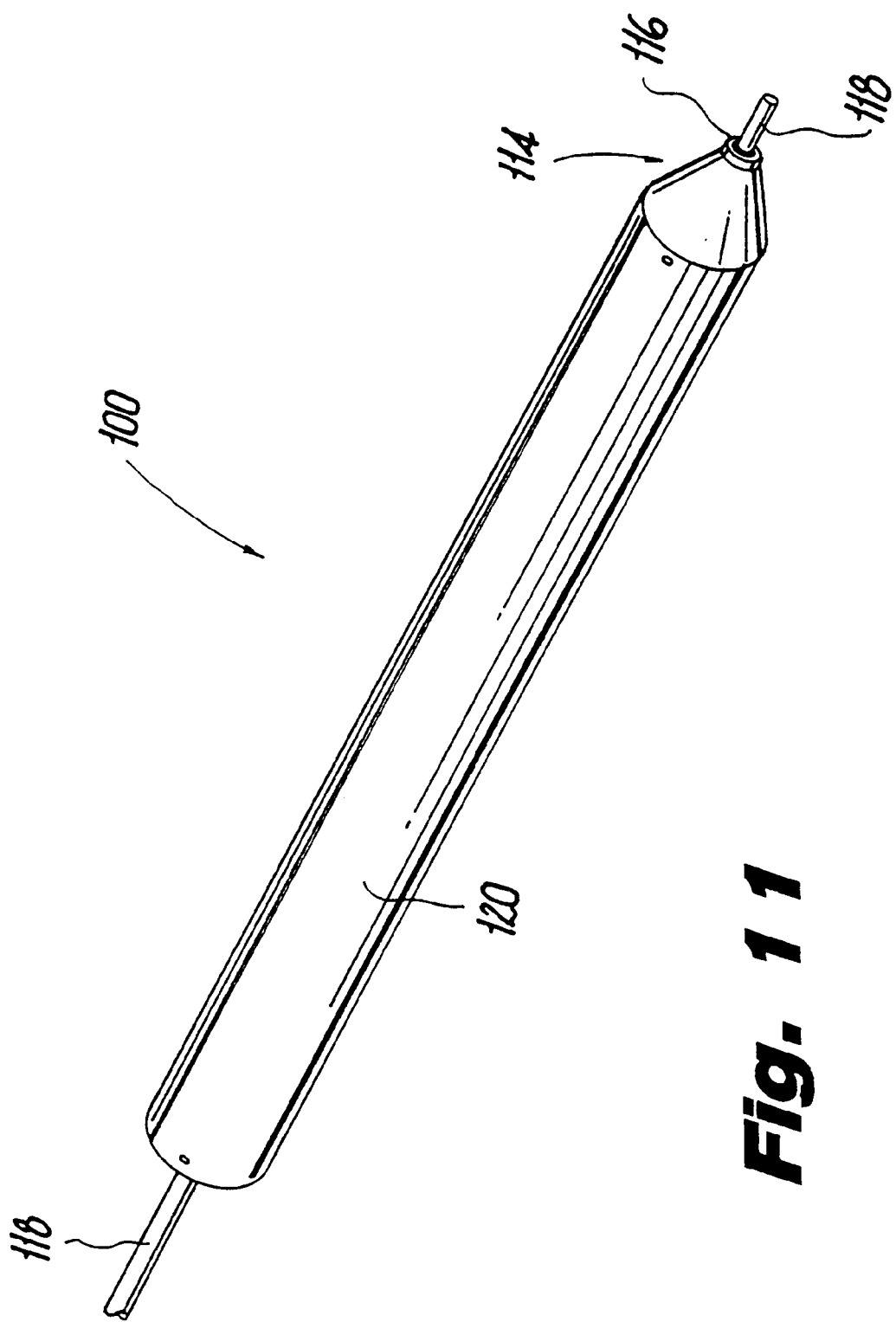
FIG. 11 illustrates a laser ablation device.

Alternate preferred embodiments of the present disclosure which create transmyocardial channels by laser ablation will now be described with reference to FIGS. 11–14. Referring to FIG. 11, there is shown a handle portion of a laser ablation device 100 which is disclosed in commonly assigned copending U.S. patent application Ser. No. 08/648,638, filed on May 13, 1996, entitled LASING DEVICE. Lasing device 100 includes a housing 120, a tapered portion 114 and a collar-like end portion 116 through which an optical fiber 118 can be advanced or retracted. Optical fiber 118 is connected on the opposite side of housing 120 to a laser energy generator (not shown) such as a xenon-chloride excimer laser energy source. In an alternate embodiment, a fiber optic bundle of a plurality of closely packed optical fibers could be utilized rather than the single fiber 118.

Housing 120 includes an advancing mechanism (not shown) operative to advance fiber 118 from collar 116 into heart tissue during a TMR procedure while laser energy is outputted therefrom. For example, laser power between about 10 mj/mm$^2$ and 60 mj/mm$^2$ may be outputted to produce transmyocardial channels while the fiber is advanced into the heart tissue at a coordinated rate. By advancing the fiber at a coordinated rate in relation to the magnitude of laser power, precise channels can be formed via ablation without mechanical tearing. Details of the advancement mechanism and of other features of laser ablation devices 100 are found in the above-noted patent application.

Figure 12A:
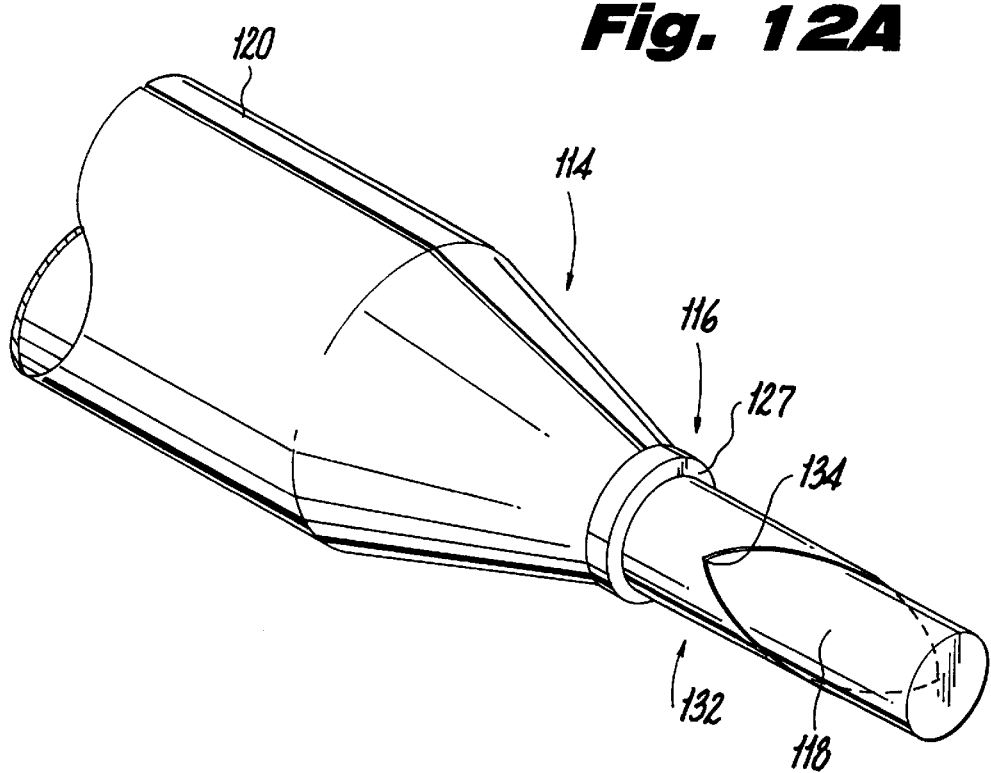
FIGS. 12A-12B show portions of a laser ablation device in accordance with the present disclosure.
Figure 12B:
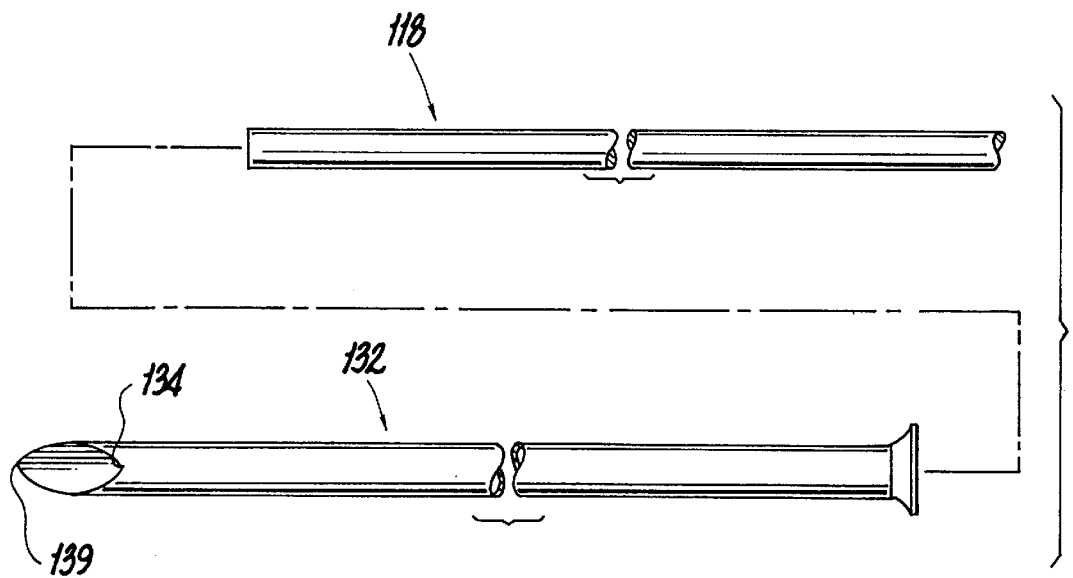

In accordance with an embodiment of the present disclosure, laser ablation device 100 is modified as shown in FIG. 12A by adding a flap creating member 132 surrounding optical fiber 118. Flap creating member 132 is preferably similar or identical to flap creating member 32 of FIGS. 4–5B and also performs an analogous function as member 32—creating a flap of heart tissue to reduce bleeding from TMR channels created by optical fiber 118. Hence, flap creating member 132 is preferably of metallic material and shaped as a tubular cylinder with a beveled cutting portion. FIG. 12B illustrates the beveled portion of member 132 having an apex 139 and trough 134. The diameter of optic fiber 118 is slightly less than the inner diameter of member 132 so that fiber 118 can move translationally with minimal friction through the throughbore of member 132.

Flap creating member 132 can preferably be automatically extracted from and retracted into housing 120 via the opening of end portion 116. It will be appreciated that one skilled in the art can incorporate an automatic retraction and extraction mechanism within housing 120, which mechanism would be trigger-actuated via one or more triggers on housing 120. Alternatively, a simpler design without an automatic retraction/extraction feature could be implemented by fabricating flap creating member 132 as an integral, stationary extension of end portion 116.

Figure 13:
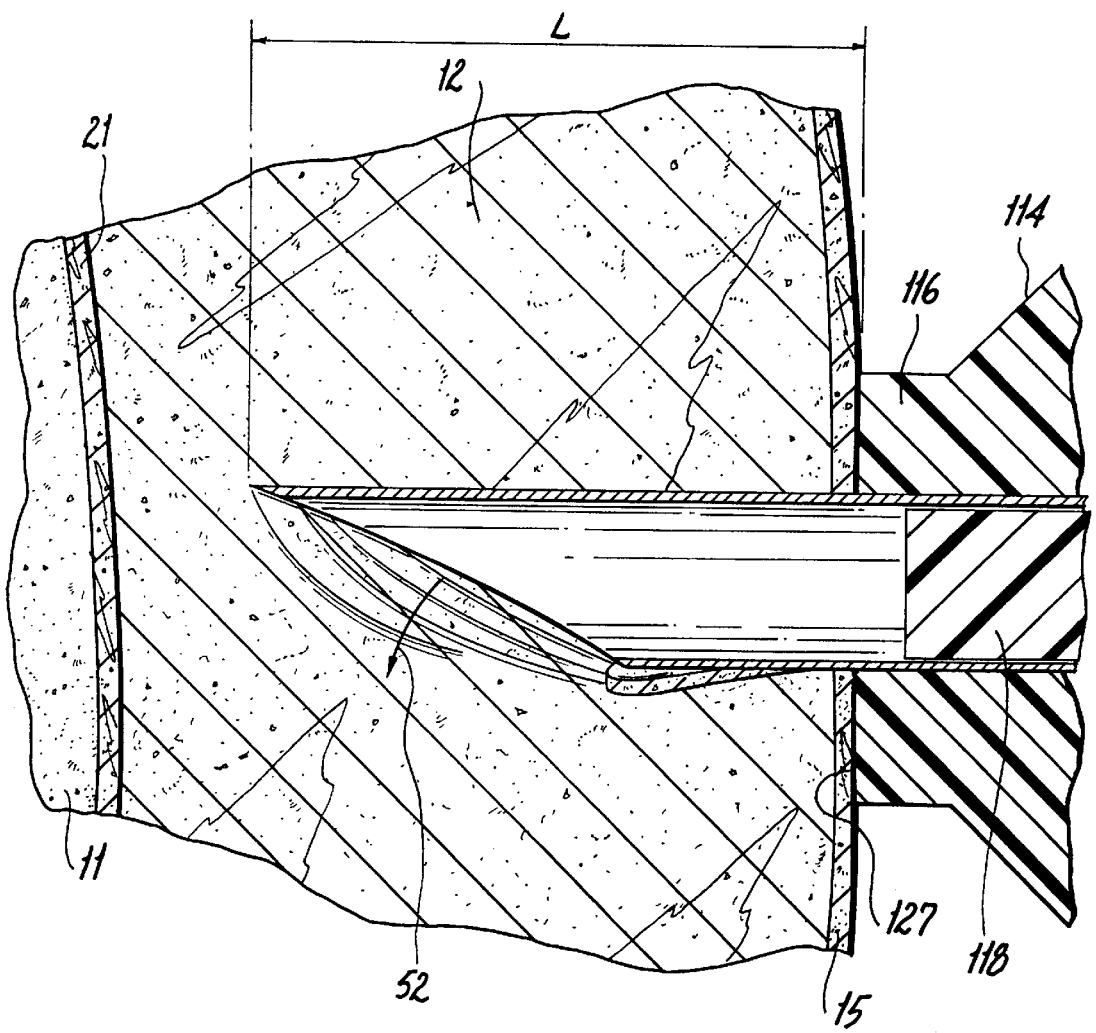
FIGS. 13-14 illustrate a laser ablation device creating a transmyocardial channel with a flap in accordance with the present disclosure.
Figure 14:
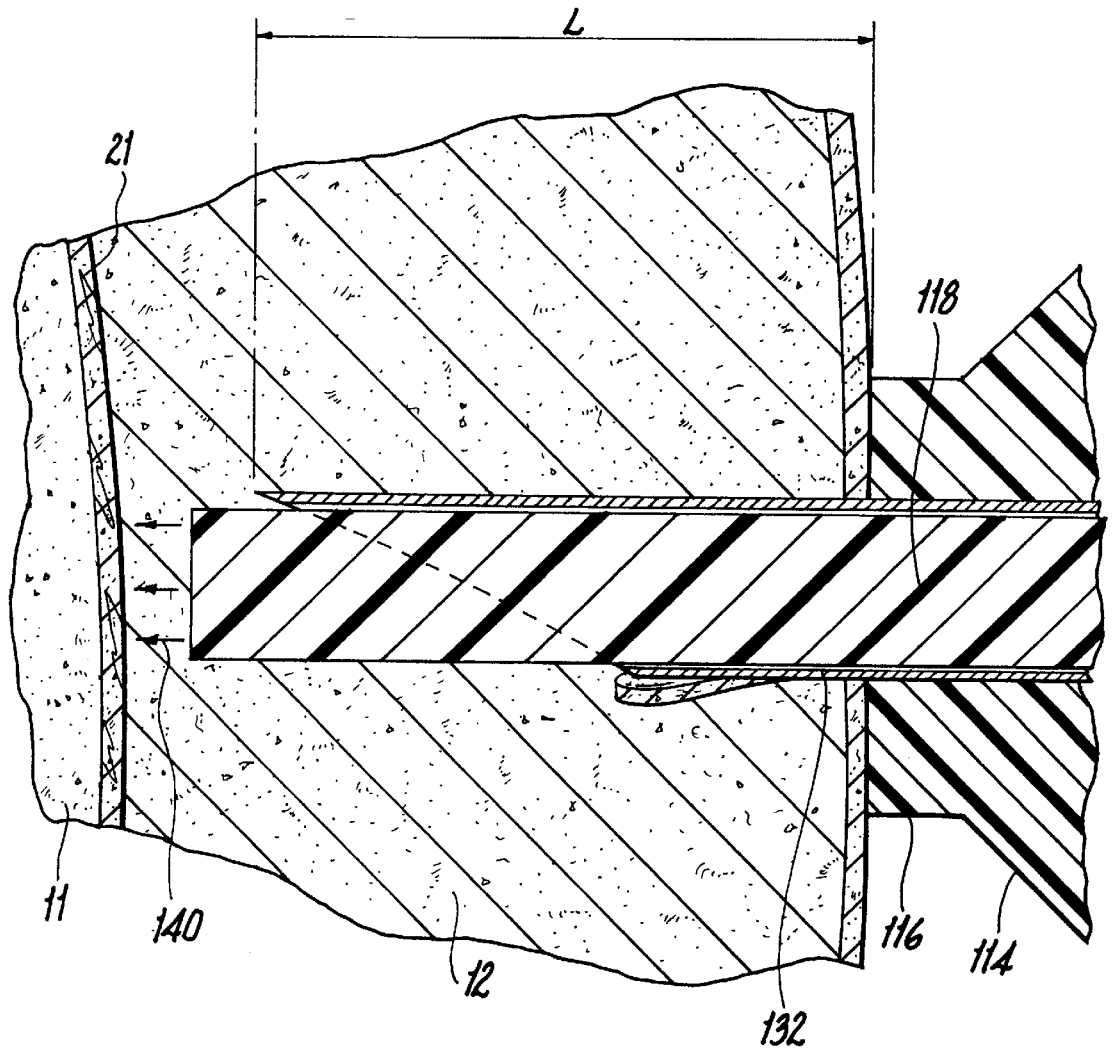

Channel formation via laser ablation is illustrated in FIGS. 13-14. Member 132 is first inserted a predetermined distance L from the outer surface of epicardium 15 into myocardium 12, where L is reliably attained by means of the annular surface 127 contacting epicardium 15 to prevent excessive penetration. Insertion of member 132 is accomplished either manually or by automatic extraction following placement of surface 127 in contact with epicardium 15. As member 132 is inserted, an annular beveled incision is made in the outer heart tissue consisting of epicardium 15 and myocardium 12, and the heart tissue separated by the incision is pushed aside in direction 52.

As shown in FIG. 14, once flap creating member 132 penetrates to distance L, the operator initiates laser energy transmission 140 from optical fiber 118 and coordinated advancement of fiber 118 into myocardium 12 to ablate myocardial and endocardial tissue and produce the desired channel. Advancement of fiber 118 may occur either continuously as laser energy is outputted, or in discrete steps. Once fiber 118 reaches ventricle 11, it is withdrawn from the myocardium, followed by withdrawal of member 132, resulting in the channel 18 and annular flap 14 as shown in FIGS. 1 and 2. As is the case with the mechanical coring embodiment discussed above, the annular interface 16 is sufficiently narrow to enable rapid blood clotting thereat, thereby obviating or substantially reducing the time needed to apply pressure to the epicardium to seal the channel.

It will be understood that various modifications can be made to the embodiments disclosed herein. For instance, wand-type mechanical coring devices can alternatively be utilized rather than the "gun" type disclosed above. Additionally, the procedure may be performed laparoscopically with appropriate design of the mechanical coring or laser ablation devices. Therefore, the above description should not be construed as limiting, but merely as exemplifications of preferred embodiments. Those skilled in the art will envision other modifications within the scope and spirit of the claims appended hereto.

What is claimed is:

1. A method for performing transmyocardial revascularization (TMR) comprising the steps of:

creating an incision in an outer portion of heart tissue of a patient;

creating a channel in the patient's myocardium through the incision by advancing a channel creating device into the myocardium beyond the depth of the incision to remove myocardial tissue without removing all outer portion heart tissue coinciding with the channel, whereby said outer portion heart tissue that remains acts as a cap to reduce bleeding from the channel subsequent to removal of the channel creating device.

2. The method according to claim 1, wherein said step of creating a channel is performed by mechanical coring.

3. The method according to claim 1, wherein said step of creating a channel is performed by laser ablation with an advancing laser ablation member.

4. The method according to claim 1, wherein said incision is an annular incision less than 360 degrees in extent and said step of creating an incision is performed by inserting a tubular beveled cutting member within the outer portion heart tissue to enable said channel creating device to penetrate said incision and create said channel without substantially removing said outer portion heart tissue coinciding with the channel.

5. The method according to claim 1, wherein said outer portion heart tissue that remains comprises epicardial and myocardial tissue.

6. A method for performing transmyocardial revascularization (TMR) comprising the steps of:

creating an incision in an outer portion of heart tissue of a patient;

pushing aside heart tissue separated by the incision;

creating a channel in the myocardium through the incision by removing myocardial tissue using a channel creating device that advances into the myocardium beyond the depth of the incision; and after forming the channel, ceasing to push aside the heart tissue, whereby the heart tissue that was pushed aside returns to a position adjacent the incision thereby forming a flap that operates to cap the channel by preventing excessive bleeding therefrom.

7. The method according to claim 6, wherein said channel creating device comprises a mechanical coring device.

8. The method according to claim 6, wherein said channel creating device comprises a lasing device.

9. The method according to claim 6, wherein:

the steps of creating an incision and pushing aside heart tissue are performed substantially contemporaneously by incising the heart tissue via insertion of a beveled cutting end of a tubular cutting member a predetermined distance into the myocardium, said cutting end pushing aside epicardial and myocardial tissue while incising; and said step of ceasing to push aside heart tissue comprises removing said cutting end from the heart tissue after the channel is formed to create a flap of myocardial and epicardial tissue that operates to cap the channel.

10. The method according to claim 9, wherein said channel forming device comprises a mechanical coring device having a hollow cylindrical channel coring member disposed within said tubular cutting member, and said step of creating a channel comprises advancing said coring device through said cutting member as said cutting member is held substantially stationary at said predetermined distance into the myocardium.

11. The method according to claim 7, wherein said mechanical coring device has a linearly advanceable, rotating coring member and wherein said channel is formed by simultaneously advancing and rotating the coring member at predetermined coordinated rates to core myocardial tissue.

12. The method according to claim 6, wherein said channel is formed having a diameter in the range of about 0.1 mm to about 5 mm.

13. The method according to claim 12, wherein said channel is formed having a diameter of about 2 mm.

14. The method according to claim 8, wherein said lasing device includes an optical fiber for transmitting laser energy to ablate and thereby remove said myocardial tissue, said optical fiber being advanced through the incision and the myocardium at a rate coordinated with laser energy outputted from said optical fiber to ablate heart tissue and create said channel.

* * * * *